(12) United States Patent
Whitt et al.

(10) Patent No.: US 11,147,317 B2
(45) Date of Patent: Oct. 19, 2021

(54) UNDERGARMENT WITH A WATERPROOF POCKET AND AN ABSORBENT INSERT

(71) Applicants: Linda Whitt, Cincinatti, OH (US); Harold Lockett, Cincinatti, OH (US)

(72) Inventors: Linda Whitt, Cincinatti, OH (US); Harold Lockett, Cincinatti, OH (US)

(*) Notice: Subject to any disclaimer, the term of this patent is extended or adjusted under 35 U.S.C. 154(b) by 410 days.

(21) Appl. No.: 16/231,924

(22) Filed: Dec. 24, 2018

(65) Prior Publication Data

US 2020/0196680 A1   Jun. 25, 2020

(51) Int. Cl.
| | |
|---|---|
| *A61F 13/505* | (2006.01) |
| *A41B 9/00* | (2006.01) |
| *A41B 9/02* | (2006.01) |
| *A61F 13/66* | (2006.01) |
| *A61F 13/15* | (2006.01) |

(52) U.S. Cl.
CPC .............. *A41B 9/004* (2013.01); *A41B 9/023* (2013.01); *A41B 9/026* (2013.01); *A61F 13/15203* (2013.01); *A61F 13/505* (2013.01); *A61F 13/665* (2013.01); *A41B 2300/22* (2013.01); *A41B 2300/332* (2013.01); *A41B 2400/60* (2013.01); *A61F 2013/15146* (2013.01)

(58) Field of Classification Search
CPC ........... A41B 9/004; A41B 9/02; A41B 9/023; A61F 13/4915; A61F 13/505; A61F 13/68; A61F 13/70; A61F 13/72; A61F 13/74; A61F 13/75; A61F 13/78; A61F 2013/5055; A61F 5/44; A61F 5/4401; A61F 5/451; A61F 5/453
See application file for complete search history.

(56) References Cited

U.S. PATENT DOCUMENTS

| | | | | |
|---|---|---|---|---|
| 4,414,971 A | * | 11/1983 | Chung ...................... | A61F 5/40 2/405 |
| 4,695,279 A | * | 9/1987 | Steer ..................... | A61F 5/4401 2/406 |
| 5,875,495 A | * | 3/1999 | Thrower ................ | A41B 9/023 2/403 |
| 6,932,800 B2 | * | 8/2005 | LaVon .............. | A61F 13/15203 604/385.01 |
| 8,696,642 B1 | * | 4/2014 | Price ................... | A61F 13/4915 604/385.09 |

(Continued)

*Primary Examiner* — Catharine L Anderson
(74) *Attorney, Agent, or Firm* — Lyman Moultan, Esq.; Moulton Patents, PLLC

(57) ABSTRACT

An absorbing undergarment includes a waterproof pocket configured to attach to a front side of an undergarment. The waterproof pocket includes a sealable opening to receive an absorbent insert and an orifice adjacent an undergarment opening for urine to pass there through. A front panel of the undergarment is designed to attach to the waterproof pocket so the pocket orifice aligns to a front opening of the undergarment. An absorbent insert is designed in shape to be complementary to a shape of the waterproof pocket to maximize surface area. The absorbent insert is urine retentive. A self-sealing opening for a male genitalia portion to pass there through is also included. The waterproof pocket flays open like a butterfly's wings attached at a crotch of the undergarment and is fastened around a perimeter thereof. The sealable opening includes an interlocking groove and ridge that form a tight seal when pressed together.

18 Claims, 4 Drawing Sheets

(56) References Cited

U.S. PATENT DOCUMENTS

| | | | |
|---|---|---|---|
| 10,058,463 B2* | 8/2018 | Johnson | A61F 13/4915 |
| 10,849,367 B2* | 12/2020 | Brown, Sr. | A61F 13/15 |
| 2003/0028161 A1* | 2/2003 | Carballo | A61F 5/453 |
| | | | 604/349 |

* cited by examiner

UNDERGARMENT WITH A WATERPROOF POCKET AND AN ABSORBENT INSERT

BACKGROUND OF THE INVENTION

People with medical conditions which cause them to experience urinary incontinence often require diapers or similar products because they are unable to control their bladders or bowels. People who are bedridden or in wheelchairs, including those with good bowel and bladder control, may also wear diapers because they are unable to access the toilet independently. Those with cognitive impairment, such as dementia, may require diapers because they may not recognize their need to reach a toilet. Men's and women's adult diapers in the form of underpants are available for such needs.

Absorbent incontinence products come in a wide range of types (drip collectors, pads, underwear and adult diapers), each with varying capacities and sizes. The largest volume of products that is consumed falls into the lower absorbency range of products, and even when it comes to adult diapers, the cheapest and least absorbent brands are used the most. This is not because people choose to use the cheapest and least absorbent brands, but rather because medical facilities are the largest consumer of adult diapers, and they have requirements to change patients as often as every two hours. As such, they select products that meet their frequent-changing needs, rather than products that could be worn longer or more comfort.

However, it seems that none of the offered products are offering an effective and convenient relief. There are essentially two ways of providing protection for those who are unable to take care of their immediate needs: active and passive protection. Active protection includes assist devices for helping one discharge directly into a toilet or urinal. Passive protection includes baby, toddler and adult diapers.

There has therefore been a long felt need for an ergonomic and versatile protective undergarment that gives a wearer a high degree of confidence and security for everyday urinary incontinence use.

SUMMARY OF THE INVENTION

A disclosed absorbing undergarment includes a waterproof pocket configured to attach to a front side of an undergarment, the waterproof pocket comprising a sealable opening to receive an absorbent insert and an orifice adjacent an undergarment opening for urine to pass there through. A front panel of the undergarment is designed to attach to the waterproof pocket so that the orifice aligns with a front opening of the undergarment. An absorbent insert is designed in shape to be complementary to a shape of the waterproof pocket to maximize surface area, the absorbent insert configured to be urine and moisture retentive.

An undergarment for absorbing urine as disclosed includes, a waterproof pouch configured to attach to a front side of an undergarment, the pouch comprising a sealable opening to receive an absorbent insert and a self-sealing opening for a male genitalia portion to pass there through. A front panel of the undergarment configured to attach to the waterproof pouch so that the pouch self-sealing opening aligns with a front opening of the undergarment. An absorbent insert designed in shape to be complementary to a shape of the waterproof pouch to maximize surface area, the absorbent insert configured to be urine retentive.

Other aspects and advantages of embodiments of the disclosure will become apparent from the following detailed description, taken in conjunction with the accompanying drawings, illustrated by way of example of the principles of the disclosure.

Figure 1:
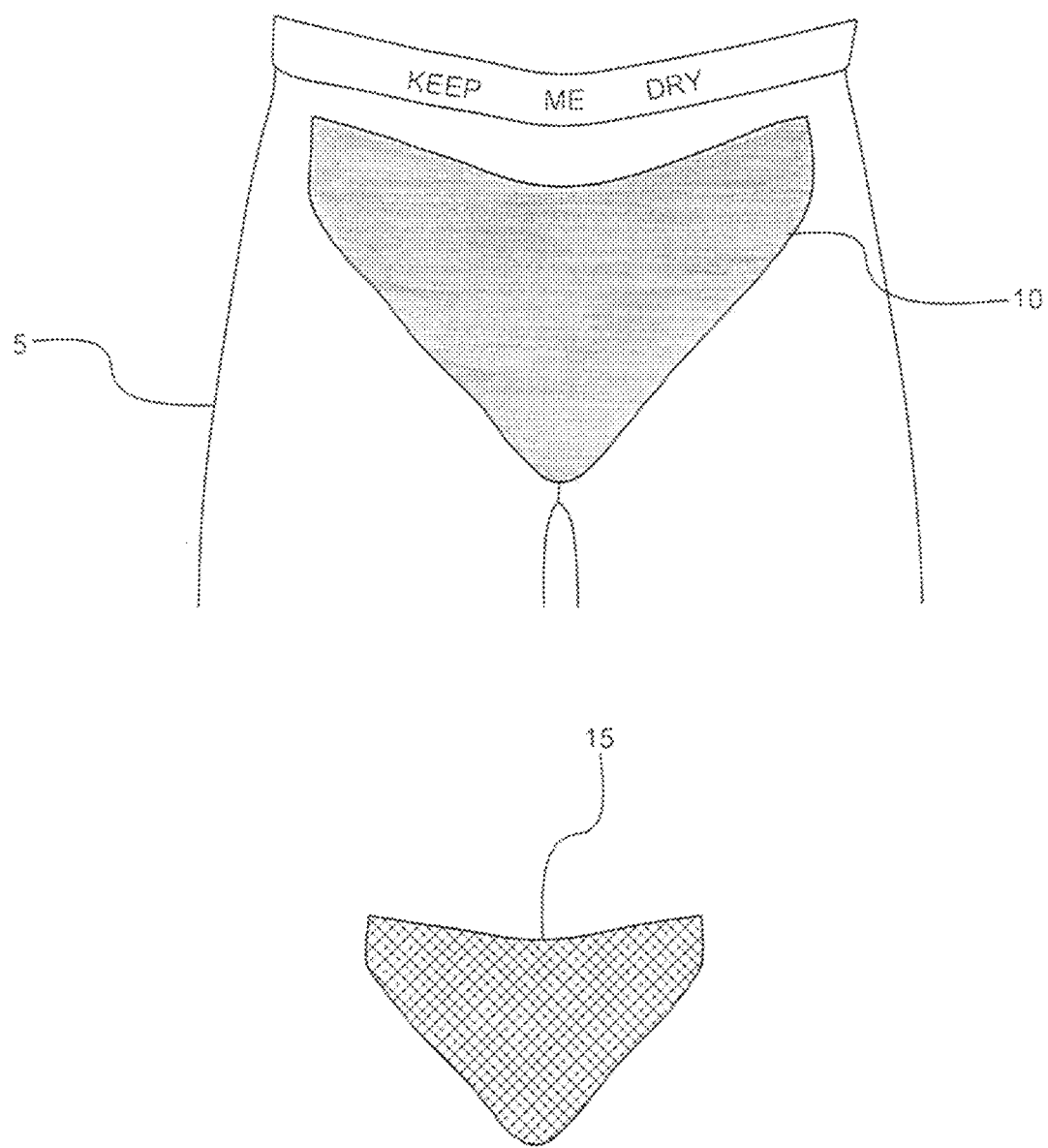
FIG. 1 is a front depiction of an undergarment with a waterproof pocket and an absorbing insert in accordance with an embodiment of the present disclosure.

Throughout the description, similar and same reference numbers may be used to identify similar and same elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the claims.

The disclosed underwear has a waterproof pocket designed to receive a disposable cotton insert to keep one dry. The cotton insert keeps the complementary outer garment dry because it keeps urine off of the skin. The outer garment includes a water proof pocket designed to allow the wearer to easily and discretely insert and remove the cotton insert therein. Rather than laundering or throwing away the entire garment, all the wearer does is remove the insert and exchange it for a new or clean insert. This prevents skin breakdown and rash because it isolates liquid waste from the skin. The disclosure is great for older men and toilet training boys. The garment is made with similar material that conventional underwear is made from with a special pocket for the insert. The insert includes a special cotton pad that will hold the urine. An edge of the waterproof pocket seals via an interlocking groove and ridge that form a tight seal when pressed together. The cotton insert may be changed via a snap enclosure designed to open up the pocket. An inside panel of the pocket includes a self-sealing opening for an insertion of a wearer's urethra there through.

FIG. 1 is a front depiction of an undergarment with a waterproof pocket and an absorbing insert in accordance with an embodiment of the present disclosure. The undergarment 5 can be a men's or a women's undergarment. The pouch 10, also known as a pocket, can be sewn into the undergarment or it can be attached thereto as discussed below.

Figure 2:
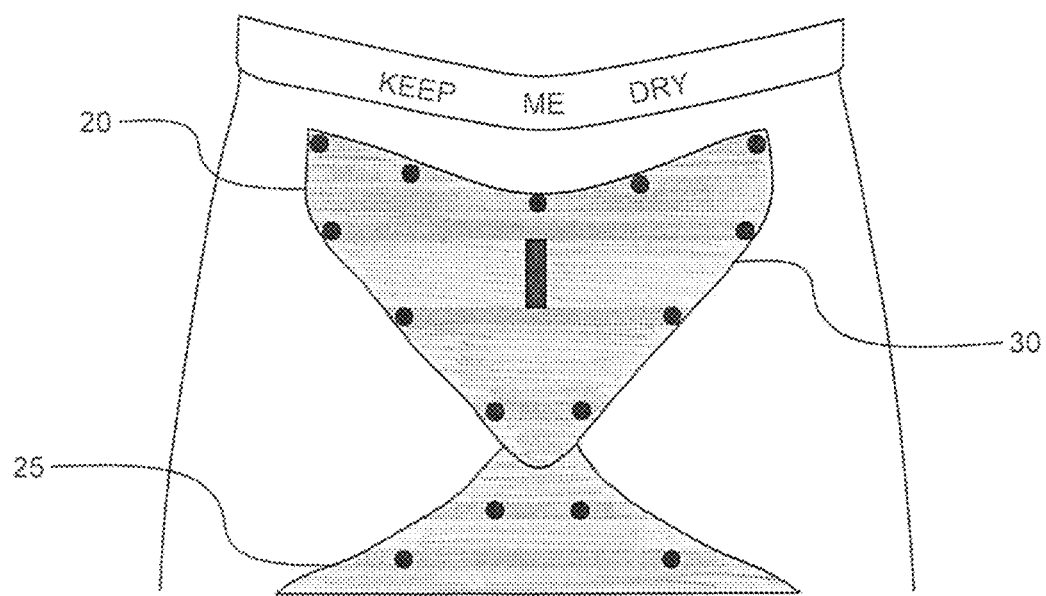
FIG. 2 is a front depiction of an undergarment with a waterproof pocket flayed open and an absorbing insert in accordance with an embodiment of the present disclosure.

FIG. 2 is a front depiction of an undergarment with a waterproof pocket flayed open and an absorbing insert in accordance with an embodiment of the present disclosure. The depiction includes the absorbent insert 15, the waterproof pouch 20, the snap close pouch 25 and the pouch orifice 30 which lines up with an opening in the undergarment typically for a men's urethra to pass for urination.

Figure 3:
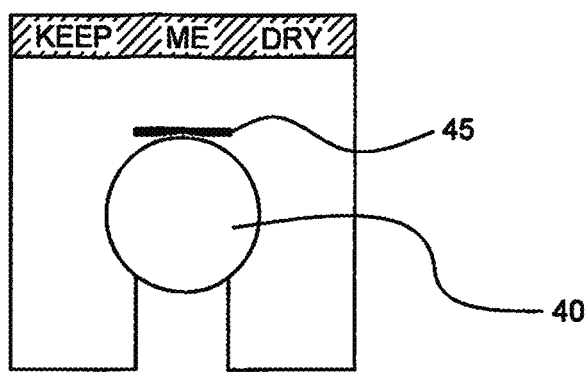
FIG. 3 is a front depiction of an undergarment with a circular waterproof pocket and sealable opening for an absorbing insert in accordance with an embodiment of the disclosure.

FIG. 3 is a front depiction of an undergarment with a circular waterproof pocket and sealable opening for an absorbing insert in accordance with an embodiment of the disclosure. Reference numbers for same and similar limitations are implicitly included. Explicitly, the depiction includes a circular waterproof pouch or pocket 40 and the resealable opening 45 for the insertion and removal of the absorbent insert (not shown).

Figure 4:
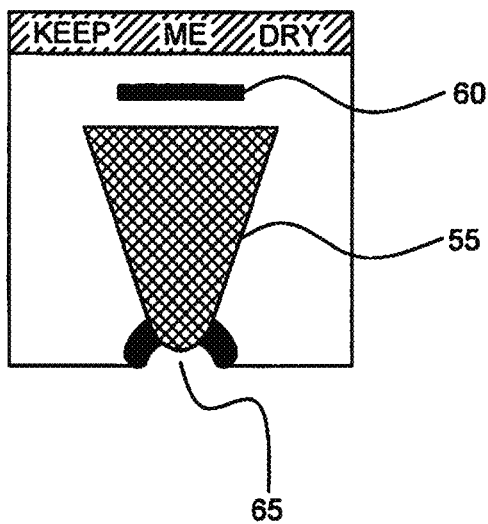
FIG. 4 is a front depiction of an undergarment with a circular waterproof pocket and sealable opening for an absorbing insert in accordance with an embodiment of the disclosure.

FIG. 4 is a front depiction of an undergarment with a circular waterproof pocket and sealable opening for an absorbing insert in accordance with an embodiment of the disclosure. Reference numbers for same and similar limitations are implicitly included. Explicitly, the depiction includes a circular waterproof pocket 55 with a fabric outside and a fabric inside for wearer comfort. Also, the resealable opening 60 is depicted for the insertion and removal of the absorbent insert (not shown).

A disclosed absorbing undergarment includes a waterproof pocket configured to attach to a front side of an undergarment, the waterproof pocket comprising a sealable opening to receive an absorbent insert and an opening adjacent an undergarment opening for urine to pass there through. A front panel of the undergarment is designed to attach to the waterproof pocket so that the pocket self-sealing opening aligns with a front opening of the undergarment. An absorbent insert is designed in shape to be complementary to a shape of the waterproof pocket to maximize surface area, the absorbent insert configured to be urine and moisture retentive.

Embodiments of the waterproof pocket are covered on an inside thereof with an undergarment cloth material similar to a material of the undergarment. Also, in the embodiments, the waterproof pocket attaches to the front panel of the undergarment via snaps. The waterproof pocket attaches to the front panel of the undergarment via a zipper. A backside of the waterproof pocket is sewn into the front panel of the undergarment in selected embodiments.

In other embodiments, the waterproof pocket flays open like a butterfly's wings attached at a crotch of the undergarment and is resealable around a perimeter thereof. The waterproof pocket sealable opening includes an interlocking groove and ridge that form a tight seal when pressed together. The waterproof pocket is shaped like an equilateral triangle extending below a crotch and proximal a waistband of the undergarment. Still yet some embodiments of the waterproof pocket are circular shaped like a target extending to a crotch and proximal a waistband of the undergarment.

An undergarment for absorbing urine as disclosed includes, a waterproof pouch configured to attach to a front side of an undergarment, the pouch comprising a sealable opening to receive an absorbent insert and a self-sealing opening for a male genitalia portion to pass there through. A front panel of the undergarment configured to attach to the waterproof pouch so that the pouch self-sealing opening aligns with a front opening of the undergarment. An absorbent insert configured in shape to be complementary to a shape of the waterproof pouch to maximize surface area, the absorbent insert configured to be urine retentive.

Embodiments of the self-sealing opening include an elasticized orifice configured to gently seal around a male genitalia portion. The insert is thicker in an area proximal the self-sealing opening. The waterproof pouch is detachable for disposal.

The disclosure offers a form-fitting and comfortable protective garment in a wide range of wearable items, including assorted types and styles of underwear, running shorts, swim trunks, traveling shorts, etc., suitable for different situations and the styles of individual users. Products of the disclosure are designed to be worn comfortably while still being able to offer relief for urinary incontinence.

The term 'garment' refers to any article of clothing worn against the body such as underwear. The pouch or pocket may come in various embodiments and dimensions, may be fabricated in one or more pieces of fabric or straps, may comprise undergarment fabric and/or regular fabric and design elements integrated directly to the panel fabric; those multiply embodiments and variations share basic characteristics of non-elastic (or very limited elasticity) structure.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Notwithstanding specific embodiments of the invention have been described and illustrated, the invention is not to be limited to the specific forms or arrangements of parts so described and illustrated. The scope of the invention is to be defined by the claims and their equivalents to be included by reference in a non-provisional utility application.

What is claimed is:

1. An absorbing undergarment, comprising:
    a waterproof pocket configured to attach to a front side of an undergarment, the waterproof pocket comprising a sealable opening to receive an absorbent insert and an orifice adjacent an undergarment opening for urine to pass there through; and
    an absorbent insert configured in shape to be complementary to a shape of the waterproof pocket to maximize surface area, the absorbent insert configured to be urine and moisture retentive,
    wherein the waterproof pocket is covered on an inside and an outside thereof with an undergarment cloth material similar to a material of the undergarment.

2. The absorbing undergarment of claim 1, wherein the waterproof pocket attaches to the front panel of the undergarment via snaps.

3. The absorbing undergarment of claim 1, wherein the waterproof pocket attaches to the front panel of the undergarment via a zipper.

4. The absorbing undergarment of claim 1, wherein a backside of the waterproof pocket is sewn into the front panel of the undergarment.

5. The absorbing undergarment of claim 1, wherein the waterproof pocket flays open like a butterfly's wings attached at a crotch of the undergarment and is resealable.

6. The absorbing undergarment of claim 1, wherein the waterproof pocket sealable opening comprises an interlocking groove and ridge that form a tight seal when pressed together.

7. The absorbing undergarment of claim 1, wherein the waterproof pocket is shaped like an equilateral triangle extending below a crotch and proximal a waistband of the undergarment.

8. The absorbing undergarment of claim 1, wherein the waterproof pocket is circular shaped like a target extending to a crotch and proximal a waistband of the undergarment.

9. An undergarment for absorbing urine, comprising:
   a waterproof pouch configured to attach to a front side of an undergarment, the pouch comprising a sealable opening to receive an absorbent insert and a self-sealing opening for a male genitalia portion to pass there through;
   a front panel of the undergarment configured to attach to the waterproof pouch so that the pouch self-sealing opening aligns with a front opening of the undergarment; and
   an absorbent insert configured in shape to be complementary to a shape of the waterproof pouch to maximize surface area, the absorbent insert configured to be urine retentive,
   wherein the insert is thicker in an area proximal the self-sealing opening.

10. The undergarment of claim 9, wherein the waterproof pouch is covered on an inside thereof with an undergarment cloth material similar to a material of the undergarment.

11. The undergarment of claim 9, wherein the waterproof pouch attaches to the front panel of the undergarment via snaps.

12. The undergarment of claim 9, wherein a backside of the waterproof pouch is sewn into the front panel of the undergarment.

13. The absorbing undergarment of claim 9, wherein the waterproof pouch flays open like a butterfly's wings attached at a crotch of the undergarment and is configured to reseal.

14. The absorbing undergarment of claim 9, wherein the waterproof pouch sealable opening comprises an interlocking groove and ridge that form a tight seal when pressed together.

15. The absorbing undergarment of claim 9, wherein the pocket is shaped like an equilateral triangle extending below a crotch and proximal a waistband of the undergarment.

16. The absorbing undergarment of claim 9, wherein the self-sealing opening comprises an elasticized orifice configured to gently seal around a male genitalia portion.

17. The absorbing undergarment of claim 9, wherein the waterproof pocket is circular shaped like a target extending to a crotch and proximal a waistband of the undergarment.

18. The absorbing undergarment of claim 9, wherein the waterproof pouch is detachable for disposal.

* * * * *